(12) United States Patent
Catel et al.

(10) Patent No.: US 11,020,323 B2
(45) Date of Patent: Jun. 1, 2021

(54) AGENT FOR CONDITIONING DENTIN AND ENAMEL

(71) Applicant: Ivoclar Vivadent AG, Schaan (LI)

(72) Inventors: Delphine Catel, Buchs (CH); Thorsten Bock, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 442 days.

(21) Appl. No.: 15/751,597

(22) PCT Filed: Aug. 12, 2016

(86) PCT No.: PCT/EP2016/069273
§ 371 (c)(1),
(2) Date: Feb. 9, 2018

(87) PCT Pub. No.: WO2017/025634
PCT Pub. Date: Feb. 16, 2017

(65) Prior Publication Data
US 2018/0228700 A1   Aug. 16, 2018

(30) Foreign Application Priority Data

Aug. 12, 2015   (EP) ..................................... 15180817

(51) Int. Cl.
*C09K 3/00* (2006.01)
*A61K 6/70* (2020.01)
*A61K 6/40* (2020.01)

(52) U.S. Cl.
CPC . *A61K 6/70* (2020.01); *A61K 6/40* (2020.01)

(58) Field of Classification Search
USPC ........................................................... 106/35
See application file for complete search history.

(56) References Cited

U.S. PATENT DOCUMENTS

| | | | | |
|---|---|---|---|---|
| 3,772,431 A * | 11/1973 | Mlkvy et al. | .......... | A61Q 11/00 424/44 |
| 4,211,682 A * | 7/1980 | Suminoe | ................ | C08L 29/04 523/109 |
| 4,964,911 A | 10/1990 | Ibsen et al. | | |
| 5,270,351 A | 12/1993 | Bowen | | |
| 5,354,827 A * | 10/1994 | Muller | ....................... | C09J 4/00 526/304 |
| 2004/0002037 A1* | 1/2004 | Orlowski | ................ | C08L 33/00 433/220 |
| 2006/0084717 A1* | 4/2006 | Cohen | ...................... | A61K 6/40 523/116 |
| 2010/0028541 A1* | 2/2010 | Nagai | .................... | C23C 22/362 427/327 |
| 2014/0140938 A1* | 5/2014 | Gallis | .................... | A01N 59/06 424/49 |
| 2014/0367613 A1* | 12/2014 | Mashio | ................ | C04B 41/009 252/301.36 |
| 2015/0231606 A1* | 8/2015 | Tsukada | ................ | B01J 35/004 502/340 |

FOREIGN PATENT DOCUMENTS

| EP | 2626057 A1 * | 8/2013 | ............... A61K 6/40 |
|---|---|---|---|
| EP | 2626057 A1 | 8/2013 | |

* cited by examiner

*Primary Examiner* — James E McDonough
(74) *Attorney, Agent, or Firm* — Ann M. Knab; Thad McMurray

(57) ABSTRACT

Aqueous solution of a transition and main group metal salt for use as conditioning agent in dental restoration therapy.

14 Claims, 11 Drawing Sheets

Solution O

Enamel (30s)

Dentin (15s)

Citrate buffer 0 h    24 h    48 h

Collagenase 0 h    24 h    48 h

2% ZrOCl$_2$

1% ZrOCl$_2$

37% H₃PO₄

Solution A

Solution B

Enamel (15s)     Enamel (30s)     Dentin (15s)

Solution D

Enamel (15s)     Dentin (15s)

Solution E

Enamel (15s)

Dentin (15s)

Solution F

Enamel (15s)

Dentin (15s)

Solution G

Enamel (15s)　　　　　　　　Dentin (15s)

Solution H

Enamel (15s)　　　　　　　　Dentin (15s)

Solution I

Enamel (15s)  Dentin (15s)

Solution J

Enamel (30s)  Dentin (15s)

Solution K

Enamel (30s)　　　　　　　　Dentin (15s)

Solution L

Enamel (30s)　　　　　　　　Dentin (15s)

Solution M

Enamel (30s)         Dentin (15s)

Solution N

Enamel (30s)         Dentin (15s)

Solution O

Enamel (30s)

Dentin (15s)

Solution P

Enamel (30s)

Dentin (15s)

Solution Q

Enamel (30s)

Dentin (15s)

AGENT FOR CONDITIONING DENTIN AND ENAMEL

CROSS-REFERENCE TO RELATED APPLICATIONS

This application is a National Stage application of International patent application PCT/EP2016/069273 filed on Aug. 12, 2016, which claims priority to European patent application No. 15180817.7 filed on Aug. 12, 2015, the disclosures of which are incorporated herein by reference in their entirety.

FIELD OF THE INVENTION

The invention relates to formulations for conditioning tooth structure (dentin and enamel) in order to achieve a durable and strong bond to dental restoration materials. The formulations are characterized by simple handling, high error tolerance and improved long-term durability of the bond.

BACKGROUND OF THE INVENTION

In the case of the machining ("drilling") of teeth, a so-called smear layer, which consists primarily of microscopic drilling debris, forms on the tooth surface. The smear layer impedes the adhesion of the materials which are used for the subsequent restoration of the tooth. The standard method for removing the smear layer is treatment of the tooth surface with 35-37% phosphoric acid. Said method is also called the "total-etch" (TE) or "etch&rinse" method. Removing the smear layer allows for contact between the dental adhesive applied subsequently and the intact and mechanically loadable tooth surface. Phosphoric acid creates a distinctive microretentive etching pattern on tooth enamel and thus permits the micromechanical adhesive bond to the adhesive system. On dentin, the conditioning agent frees the dentinal tubules from the smear layer and exposes collagen fibres. The infiltration of the tubules and the collagen fibres by the adhesive leads to a micromechanical bonding (Pashley, D. H., The evolution of dentin bonding from no-etch to total-etch to self-etch, *Adhes. Tech. Sol.* 2002, 1, 1-5).

The usual treatment procedure of direct restorative therapy with a TE adhesive provides the following work steps: (1) mechanical removal of carious tissue; (2) etching of the tooth surface with phosphoric acid; (3) rinsing off of the phosphoric acid with water; (4) removal of excess water from the cavity surface with a dental air blower ("drying"); (5) application of the adhesive; (6) blowing off the solvent; (7) light-curing of the adhesive; (8) application of the filling composite and optionally further steps for completing the restoration.

A critical step of said method is drying the tooth surface after the phosphoric acid has been rinsed off. It has been shown that the durability of the restoration depends to a large extent on the wetness of the dentin surface, irrespective of the adhesive used. In order to achieve a high level of adhesion, a certain residual wetness must be set before the application of the adhesive ("wet bonding technique"). However, because of its strong demineralizing effect, phosphoric acid exposes the collagen fibrils present in the dentin. On dentin prepared in this way, drying with an air blower for slightly too long already leads to the collapse of the exposed collagen fibrils, whereby direct contact with intact tooth structure and the infiltration by adhesive of the collagen fibres and of the tubules widened by etching is hampered. The result of this is a large reduction in the initial adhesive bond, lack of long-term durability of the dentin bond (in particular at mechanically highly loaded positions such as, e.g. structures on tooth cusps) and an increased mobility of the dentinal fluid under external stimulus and thus an increased incidence of post-operative sensitivity (Pashley, D. H., The evolution of dentin bonding from no-etch to total-etch to self-etch, *Adhes. Tech. Sol.* 2002, 1, 1-5). These problems are very unpleasant for the patient and laborious for the dentist because the patients have to be re-treated.

However, like over-drying, insufficient drying of the dentin also has negative consequences. If the adhesive is applied to dentin which is too wet there is phase separation between more and less water-compatible adhesive components. Since the usual light initiator systems are only poorly water-compatible, the polymerizability of the adhesive in water-rich phases is limited. The resulting adhesive layer is heterogeneous with respect to composition and degree of polymerization, which results in a reduced adhesive bond and insufficient sealing of the tubules.

The problem is further complicated in that the optimal wetness for achieving an ideal dentin adhesion depends strongly on the adhesive used. Despite the great importance of the total-etch protocol for restorative dentistry alternatives have therefore been intensively sought.

Another problem of the total-etch protocol are the dwell times of phosphoric acid on dentin (15 s) and enamel (30 s) which must be adhered to exactly but are different. Since the more acid-resistant enamel requires a longer contact period with phosphoric acid for conditioning, the enamel is usually treated first with phosphoric acid for 15 s and then the acid is also applied to the dentin and the treatment is continued for a further 15 s (Brady, L. A., Total-etch or self-etch: the debate continues, *DentistryIQ*, 2011).

In the case of the application of the etching agent to the enamel, above all in the case of smaller cavities, however, it is not possible to completely exclude contact with dentin, which results in too long an action of the acid on the dentin. Etching dentin for too long effects excessive widening of the dentinal tubules and strong demineralization of the dentin surface ("over-etching"). Complete sealing of greatly widened dentinal tubules with adhesive is, however, at best difficult, as is obvious from the significantly increased incidence of post-operative sensitivity after over-etching (Brady, L. A., Total-etch or self-etch: the debate continues, *DentistryIQ*, 2011).

Furthermore, it is known that phosphoric acid activates the matrix metalloproteinases (MMPs) and cysteine cathepsins occurring naturally in collagenous tissue. After the supply of adhesive, even when the supply of adhesive to the cavity has been otherwise carried out correctly, these enzymes cause the gradual degradation of the exposed collagen network. Since the collagen network occupies an appreciable volume in the adhesive layer, its degradation leaves cavities and reduces the mechanical loading capacity of the tooth-adhesive bond. Numerous in vitro investigations of the enzymatic degradation of dentinal collagen in restored tooth tissue have shown a significant reduction in the bonding effect, even after a relatively short period of time (Tjaderhane, L. et al., Optimizing dentin bond durability: Control of collagen degradation by matrix metalloproteinases and cysteine cathepsins, *Dent. Mater.* 2013, 29, 116-135).

Because of the named problems, the total-etch protocol is susceptible to application errors and often does not produce the desired result. In the hope of avoiding the disadvantages of the use of phosphoric acid, numerous alternative conditioning agents have been developed. Johnson, G. et al., Dentin bonding systems: a review of current products and techniques, *The Journal of the American Dental Association,* 1991, 122, 34-41, investigate 11 different, commercially available dentin adhesives, and v. Meerbeek, M. et al., Morphological aspects of the resin-dentin interdiffusion zone with different dentin adhesive systems, *J. Dent. Res.* 1992, 71, 1530-40, compare 27 dentin adhesives with each other. The materials described in these publications comprise, in addition to phosphoric acid, amino acids, complexing agents, inorganic or organic acids, sometimes mixed with metal salts, for the pre-treatment of the tooth surface.

Depending on the type of the acid, further additives, concentration and duration of application, these alternative conditioning agents sometimes have positive effects on the dentin morphology. However, in comparison with phosphoric acid, they usually lead to a poorer conditioning of enamel, which results in a less durable adhesive bond between adhesive and enamel. As is familiar to a person skilled in the art, this is normally accompanied by a reduced marginal seal quality and a reduced longevity of the restoration. To achieve a strong enamel adhesion and a high enamel margin quality, the total-etch technique using phosphoric acid therefore still represents the most effective method (Lopes, G. C. et al.; Enamel acid etching: a review, *Compend. Contin. Educ. Dent.* 2007, 28, 662-669).

SUMMARY OF THE INVENTION

The object of the invention is to provide conditioning agents for the treatment of teeth which provide results which are comparable to the total-etch method using phosphoric acid with respect to enamel adhesion and marginal seal quality, but which do not have the above-described disadvantages of said method. In particular, the agents are to yield a high level of adhesion irrespective of the degree of residual wetness of the tooth surface and not to induce the degradation of collagen. In addition, the agents are to be able to be used simultaneously on tooth enamel and on dentin without the need to observe different exposure times. Finally, the agents are not to cause the occurrence of post-operative sensitivity through the over-etching of dentin.

BRIEF DESCRIPTION OF THE DRAWINGS

Other advantages, details and characteristics can be seen from the following description and drawings wherein

FIG. 3 shows that the degradation of the collagen matrix was practically completely inhibited by the zirconium salt.

DETAILED DESCRIPTION

Figure 1:
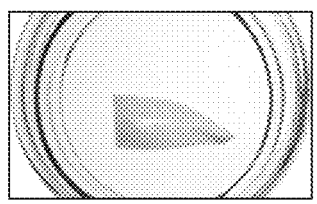
FIG. 1 shows a demineralized tooth slice immediately after the preparation, after 24 hours and after 48 hours of storage. After the demineralization with acid, the collagen matrix of the tooth remains. This did not change during storage, i.e. the collagen was not degraded by the demineralization.
Figure 1:
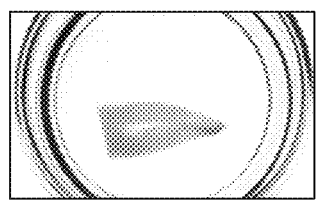
Figure 1:
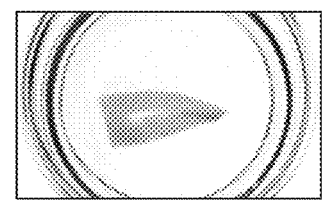

This object is achieved according to the present invention by aqueous solutions which comprise at least one salt of a transition metal and/or one salt of a main group metal. According to the present invention, metals of the fourth to sixth periods of the periodic table of elements are preferred. It was surprisingly found that such solutions are suitable for use as conditioning agents in the case of dental restoration therapy.

According to the present invention, by a conditioning agent for dental restoration therapy is meant an agent that can be applied directly to the tooth surface, i.e. to the tooth enamel and/or the dentin, and in particular to the smear layer present after machining of the tooth, and that prepares the tooth surface for the application of subsequent dental restoration materials, such as e.g. adhesives, by improving the adhesion of these materials to tooth enamel and/or dentin.

It was found that aqueous solutions of transition metal and main group metal salts are capable of etching the tooth structure and of dissolving the smear layer at least partially, even without the addition of inorganic or organic acids.

According to the present invention, solutions of salts of polyvalent metals are preferred, in particular of metal salts in which the metals have a valency of +2 and in particular +3 or +4. Particularly preferred are salts of metals of group 4 (CAS group IV B) as well as of main groups 14 and 15 (CAS groups IV A and V A) of the periodic table of elements, quite particularly preferred are the salts of $Zr^{4+}$, $Hf^{4+}$, $Sn^{4+}$ and $Bi^{3+}$ and $Ti^{4+}$ and in particular salts of $Zr^{4+}$, $Hf^{4+}$, $Sn^{4+}$ and $Bi^{3+}$. Of these the salts of $Zr^{4+}$, $Hf^{4+}$, $Bi^{3+}$ and $Ti^{4+}$ and in particular salts of $Zr^{4+}$, $Hf^{4+}$, and $Bi^{3+}$ are most preferred. The salts can be used alone or as a mixture of two or more of said salts.

In all cases, those metal salt solutions are quite particularly preferred according to the present invention that contain no added acid in addition to the metal salts, wherein by acids is meant Brønsted acids, i.e. proton-donating acids with a pK value <9. The metal salt solutions according to the present invention thus preferably contain no mineral acids, no phosphoric acid and no organic acids such as carboxylic, phosphonic and sulphonic acids.

The metal salts used according to the present invention are preferably the salts of strong acids, in particular of mineral acids, i.e. they preferably contain as anions $Cl^-$, $Br^-$, $I^-$, $NO_3^-$, $SO_4^{2-}$, optionally as mixed salts with oxoanions.

In general, those salts are preferred that contain no anions which impede the formation of aqua complexes or the achievement of homogeneous solutions in the desired concentration range or that have a buffering effect. The solutions according to the present invention thus preferably contain no EDTA, no nitrilotriacetic acid (NTA), no formate, acetate, carbonate, hydrogen carbonate and no salts of acids with a pKa value >3.

Particularly suitable transition and main group metal salt solutions according to the present invention are solutions of $SnCl_4$ and in particular of $ZrOCl_2$, $ZrO(NO_3)_2$, $Zr(SO_4)_2$, $Hf(SO_4)_2$, $HfCl_4$, $Hf(NO_3)_4$, $TiOSO_4$, $Bi(NO_3)_3$ or mixtures thereof.

In addition to the above-named metal salts, the transition and main group metal salt solutions according to the present invention can preferably additionally comprise one or more salts of other main group and/or transition metals, wherein in the case of main group metals salts of metals with a valency of +2 to +3 are particularly preferred and in the case of transition metals metals with a valency of +2 are particularly preferred. Quite particularly preferred are salts of aluminium, copper or zinc, in particular salts of $Cu^{2+}$, $Zn^{2+}$ and $Al^{3+}$, such as e.g. $Al(NO_3)_3$, $CuSO_4$ and $ZnSO_4$. It was found that these metals strengthen the effectiveness of the solutions against MMPs. The metal salt solutions can advantageously also comprise a tin salt as an additional metal salt, preferably a salt of $Sn^{4+}$, more preferably $SnCl_4$. The use of tin salts as additional salts implies that the metal salt solutions must comprise at least one further metal salt.

According to a particularly preferred embodiment, the formulation according to the present invention consists substantially of an aqueous or aqueous-organic solution of one or more salts of transition and main group metals and contains no additions of acids, such as organic or inorganic acids.

It was found that the metal salt solutions used according to the present invention are capable of etching dentin and tooth enamel and of dissolving the smear layer totally or partially. The exact reason for this effect is not known. It is assumed that the metal salts form so-called aquo complexes in aqueous solution, i.e. complexes which contain at least one water molecule as ligand, and that these complexes react acidically by donating $H^+$ in accordance with reaction equation (1):

$$Me(H_2O)^{n+} + H_2O \rightleftharpoons Me(OH)^{(n-1)+} + H_3O^+ \qquad (1)$$

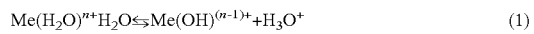

According to the present invention, salts of those transition and main group metals are therefore preferred that form aquo complexes, in particular those that form aquo complexes with a pKa value in aqueous solution at 25° C. of −2 to +4 ($Bi^{3+}$, $Sn^{4+}$, $Hf^{4+}$, $Zr^{4+}$, $Ti^{4+}$), preferably −1 to +2 ($Bi^{3+}$, $Hf^{4+}$, $Zr^{4+}$) (see S. J. Hawkes, Journal of Chemical Education, Vol. 73, No. 6, (1996), 516-517).

The metal cation Me determines by means of its charge density the polarization of the co-ordinated water and thus the acidity of the salt solution. According to the present invention, transition metal salts that contain metal cations with a high charge, i.e. at least divalent metal cations ($Me^{2+}$), particularly preferred are tri- or tetravalent metal cations ($Me^{3+}$ or $Me^{4+}$).

The protons donated in (1) are presumed to effect the dissolution of the hydroxylapatite from tooth enamel, dentin and smear layer in accordance with reaction equation (2):

$$Ca_5(PO_4)_3OH + H_3O^+ \rightleftharpoons 5Ca^{2+} + 3PO_4^{3-} + 2H_2O \qquad (2)$$

The released phosphate anions can then form phosphates with the metal cations of the transition metal salt in accordance with reaction equation (3) (for example for Me=$Zr^{4+}$):

$$3Zr(OH)^{3+} + 4PO_4^{3-} \rightarrow Zr_3(PO_4)_4 + 3OH^- \qquad (3)$$

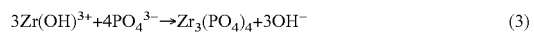

According to the present invention, those transition metal salts are preferred the metal cations of which form phosphates of low solubility, i.e. phosphates which precipitate under the conditions of use. Here, of low solubility means a solubility product in water at 20° C. of <$10^{-4}$, preferably of <$10^{-6}$, particularly preferably of <$10^{-8}$.

The absence of added acids, in particular of phosphoric acid or polydentate organic acids such as oxalic, maleic or citric acid, increases the activity of the metal ion and thus promotes the formation of metal phosphates of low solubility. This is a reason why the solutions according to the present invention preferably contain no added acids or complexing agents such as EDTA.

Precipitation of the phosphate ions shifts the equilibrium according to reaction equation (2) towards the right and thus promotes the dissolution of the tooth enamel which can only be etched with difficulty. The reaction ends when the conditioning agent is used up.

Despite the good etching effect on enamel it was surprisingly found that the transition and main group metal salt solutions used according to the present invention do not lead to an over-etching of the dentin. It is assumed that, by means of binding to co-ordinating groups of the collagen, such as e.g. —OH, —COOH, —CONH— or —NH$_2$, the transition metal salts lead to a cross-linking of the collagen debris present in the smear layer and thus regions with increased protein content (e.g. the internal volume of the dentinal tubules filled with smear layer) are less strongly etched. The diffusion-driven reaction of the etching agent with the mineral phase of the dentin is slowed down by the loosely adhering metal salt-collagen layer which is removed by the rinsing. By this means, an over-etching of the more sensitive dentin is prevented and the risk of post-operative sensitivity is significantly reduced, while the desired stronger etching effect occurs on the collagen-free tooth enamel.

The absence of inorganic or organic acids and of chelating agents is also advantageous with respect to the collagen cross-linking because said acids and chelating agents impede the reaction of the metal cations with the functional groups of the collagen.

By means of the choice of the metal salts and the concentrations thereof, the activity of the solution according to the present invention during tooth conditioning can be adjusted in accordance with equations (1) and (3).

Surprisingly, the etching of dentin with the metal salt solutions according to the present invention leads to a noticeably increased resistance to over-drying. In clinical use this represents a very advantageous increase in the technical tolerance in comparison with the established phosphoric acid conditioning. It is assumed that an ionic cross-linking of the collagen fibres with transition and main group metal salts during the etching process is also responsible for this, which stabilizes the collagen fibres against collapse in the case of over-drying.

Furthermore, it was found that the transition and main group metal salt solutions according to the present invention do not lead to an activation of matrix metalloproteinases or cysteine cathepsins. Rather, the use of the metal salt solutions reduces the MMP activity and thus increases the long-term durability of the dentin bond. This is presumably also due to an interaction of the transition and main group metal salts with dentin proteins. The binding of metal ions and in particular of polyvalent metal ions to proteins such as collagen or collagen-borne enzymes can effect a durable change in the tertiary structure thereof by means of the introduced charge. In the case of matrix metalloproteinases or cysteine cathepsins in particular contact with the polyvalent metal salts preferred according to the present invention leads in any case to a drastic reduction or even to a complete loss of activity, which is due to a change in the tertiary structure.

The metal salts used according to the present invention and in particular the metal salts preferred according to the present invention are very biologically compatible and have no intrinsic colour. They do not form coloured deposits on the tooth, as is often the case with chromium, nickel, iron, osmium, vanadium or silver salts. In addition, the salts are sufficiently soluble in solvents or solvent mixtures which are suitable for intraoral use.

According to the present invention, solutions are preferred which comprise 0.5 to 25 wt.-%, particularly preferably 2 to 15 wt.-% and quite particularly preferably 4 to 10 wt.-% transition and/or main group metal salt(s), in particular $ZrOCl_2$, $ZrO(NO_3)_2$, $Zr(SO_4)_2$, $Hf(SO_4)_2$, $HfCl_4$, $Hf(NO_3)_4$, $TiOSO_4$, $Bi(NO_3)_3$, $SnCl_4$ or mixtures thereof.

The metal salts named as possible additions in particular of the metals $Cu^{2+}$, $Zn^{2+}$ and $Al^{3+}$ are preferably introduced in concentrations of from 0.01% to 5%.

In addition, the solutions according to the present invention comprise at least one solvent, i.e. water or a mixture of water and organic solvent. The addition of one or more organic solvents can be advantageous e.g. in order to improve the surface wetting, the stability of the formulation and/or the rinsability. Preferred organic solvents are glycerol, ethanol, ethylene glycol, propylene glycol, propanediol, butanediol, polyethylene glycol and mixtures thereof, in particular glycerol.

Particularly preferred are solutions which comprise 2 to 15 wt.-% transition and/or main group metal salt, 36 to 98 wt.-% water and 0 to 49 wt.-% organic solvent, or solutions which comprise 4 to 10 wt.-% transition and/or main group metal salt, 42 to 96 wt.-% water and 0 to 48 wt.-% organic solvent.

The etching agents according to the present invention can, moreover, advantageously comprise one or more additives, such as thickeners, dyes, antibacterial agents, preservatives, flavourings, scents and flow aids.

Thickeners serve to set an easily manageable consistency which allows for a drip-free and pinpoint application to the tooth. Thickeners can be selected from inorganic or organic materials. Preferred inorganic materials are nanoparticulate fumed silicas, such as e.g. aerosils. Preferred organic materials are cellulose derivatives, associative thickeners based on polyurethane, and polyethylene oxide. Mixtures of organic and inorganic thickeners can also be used. Preferred thickeners are polyethylene oxides, silicas and in particular mixtures thereof.

Dyes serve for easy detectability of the etching agent on the tooth in order to be able to localize the treated surface and to ensure a complete removal of the etching agent during rinsing. The colorants must be able to be easily and completely removed when the etching agent is rinsed off. Dyes can consist of inorganic or organic compounds. In particular pigments, e.g. cobalt spinels, come into consideration as inorganic dyes. Preferred organic dyes are soluble compounds, such as e.g. methylene blue, and dispersible pigments, such as e.g. copper phthalocyanine.

The additives are optionally added in an amount which is required to achieve the desired effect, that is e.g. to set a particular viscosity or colour.

The dental materials according to the present invention are suitable primarily for conditioning the surface of natural teeth (dentin and tooth enamel). This is a therapeutic use which is typically carried out intraorally by the dentist. Exemplary uses are the conditioning of the tooth surface before the application of dental cements, filling composites, coating materials and veneering materials, in particular the conditioning of the tooth surface in the case of dental restoration therapy, i.e. in the case of the restoration of damaged teeth, e.g. in the case of restorative filling therapy. The invention also relates to the use of the metal salt solutions according to the invention for the intraoral and extraoral etching of the tooth surface as well as to their use for inactivation of matrix metalloproteinase(s) and/or cysteine cathepsin(s) during tooth treatment.

The use of the solutions according to the present invention is carried out in a manner comparable to known etching agents based on phosphoric acid.

The restorative filling therapy preferably comprises the following method steps:
(1) Preparation of the carious lesion by means of mechanical excavation of the demineralized tissue.
(2) Application of the conditioning agent according to the present invention to the tooth surfaces to be adhesively bonded, e.g. with a brush-like dental applicator ("microbrush") or, in the case of paste-like formulations, with a syringe. Here, the conditioning agent is applied only to the tooth; it is not necessary to move the agent during the dwell time.

(3) After the scheduled dwell time (5-120 s, preferably 10-90 s, particularly preferably 15-60 s), the conditioning agent is rinsed off the tooth surface with a jet of water. Unlike in the case of phosphoric acid, a difference in dwell time for enamel and dentin in order to avoid over-etching of the dentin is not necessary. The dwell time on dentin, unlike in the case of phosphoric acid, also does not need to be strictly limited in order to avoid over-etching. An equally long dwell time on enamel and on dentin is preferred since this is the easiest to achieve in day-to-day clinical work.

(4) The tooth surface is dried with a stream of air until the etched enamel assumes a chalky-white appearance. In this work step, dentin which was etched with phosphoric acid is often over-dried, with the result that the collagen fibrils collapse. Therefore, in the conventional procedure, after the blow-drying, the dentin is often selectively wetted again e.g. with a wet microbrush. When the etching agent according to the present invention is used, a re-wetting of the dentin after the blow-drying is not necessary.

(5) A dental adhesive is applied to the etched tooth surface.

(6) The adhesive is blown with a stream of air and then cured e.g. with light.

(7) A filling composite suitable for the adhesive and the type of filling is introduced into the cavity and light-cured.

Any commercially available dental adhesive can be used as adhesive. It is used in accordance with the instructions for use. This method is also a subject of the invention.

The etching agents according to the present invention are suitable for all dental uses in which phosphoric acid is usually used as etching agent. Further therapeutic uses in which the metal salt solutions according to the present invention can advantageously be used as conditioning agent are:

The securing of fixed prosthodontics by means of adhesive cementing of pre-fabricated metallic, ceramic or polymeric restorations such as crowns, bridges, inlays, onlays. Here, the process is as described above except that after the adhesive treatment (conditioning) is finished a restoration is secured to the tooth by means of a cement or securing composite of low viscosity. The curing of the securing composite takes place in the usual manner, e.g. by means of self- or light-curing.

Preventive measures, such as the sealing of tooth fissures. In the case of the sealing of occlusal tooth fissures, the metal salt solution is applied to the tooth and, after the rinsing off of the etching agent and blow-drying of the tooth surface, a free-flowing fissure-sealant, e.g. a methacrylate-based free-flowing composite material, is applied and then cured.

Orthodontic measures, such as the securing of brackets or dental braces. Here, the metal salt solution is applied to the relevant part of the tooth and, after the rinsing off of the etching agent and blow-drying of the tooth surface, a special securing composite is used with which a metallic or ceramic wire retainer is secured on the tooth. The securing composite is then cured.

The metal salt solutions according to the present invention can also be used extraorally, i.e. not therapeutically, for example for pre-treating the surface of dental restorations such as prostheses, artificial teeth, inlays, onlays, crowns and bridges. This pre-treatment serves e.g. to improve the adhesion in the case of the adhesive securing and/or to clean the surfaces, e.g. by removing proteinaceous impurities in particular from glass ceramic restorations.

The invention is explained in more detail below by means of the following examples.

EXAMPLES

Example 1

Preparation of Conditioning Agents

By mixing the components, transition metal solutions with the composition indicated in Table 1 were prepared.

TABLE 1

Composition of the conditioning agents

| | | Composition (wt.-%) | |
|---|---|---|---|
| Solution | Metal salt | Solvent | Thickener/Additive |
| A | $ZrOCl_2$ (4%) | $H_2O$ (48%) glycerol (48%) | — |
| B | $Zr(SO_4)_2$ (4%) | $H_2O$ (48%) glycerol (48%) | — |
| C | $Zr(SO_4)_2$ (4%) | $H_2O$ (96%) | — |
| D | $ZrO(NO_3)_2$ (4%) | $H_2O$ (48%) glycerol (48%) | — |
| E | $ZrO(NO_3)_2$ (6%) | $H_2O$ (47%) glycerol (47%) | — |
| F | $ZrO(NO_3)_2$ (10%) | $H_2O$ (45%) glycerol (45%) | — |
| G | $ZrO(NO_3)_3$ (15%) | $H_2O$ (42.5%) glycerol (42.5%) | — |
| H | $ZrO(NO_3)_3$ (10%) | $H_2O$ (45%) PEG 400 (45%) | — |
| I | $ZrO(NO_3)_2$ (10%) | $H_2O$ (42.75%) glycerol (42.75%) | hydroxyethyl cellulose (Cellosize QP-30000H) (2%) polyurethane system (Tafigel Pur 61) (2%) pigment (Sicopal Blue K6210) (0.5%) |
| J | $TiOSO_4$ (0.5%) | $H_2O$ (49.75%) glycerol (49.75%) | — |
| K | $SnCl_4$ (4%) | $H_2O$ (96%) | — |
| L | $Bi(NO_3)_3$ (2%) | $H_2O$ (98%) | — |
| M | $Hf(SO_4)_2$ (4%) | $H_2O$ (96%) | — |
| N | $HfCl_4$ (4%) | $H_2O$ (96%) | — |
| O | 6% $ZrO(NO_3)_2$ 4% $ZnSO_4$ | $H_2O$ (90%) | — |
| P | 6% $ZrO(NO_3)_2$ 4% $CuSO_4$ | $H_2O$ (90%) | — |
| Q | 6% $ZrO(NO_3)_2$ 4% $Al_2(SO_4)_3$ | $H_2O$ (90%) | — |

Example 2

Determination of the Dentin Adhesion

The determination of the adhesion to tooth structure was carried out following the Ultradent protocol (ISO 29022). For this, solutions A-Q according to the present invention were in each case applied to the prepared tooth surface. Bovine front teeth which were embedded in a cold-curing polyester-styrene resin up to the enamel-dentin junction after removal of the pulp and the tooth neck served as test substrate. Immediately prior to the preparation of the test bodies, the embedded tooth was ground with a grinding machine plane-parallel with respect to the cylinder faces with P120 SiC abrasive paper accompanied by water cooling. By means of regular visual inspection it was ascertained that the dentin layer was exposed. The sample was then ground with P400 SiC abrasive paper until no more traces of the P120 grinding step were visible. The tooth surfaces ground with P400 paper were then rinsed under flowing lukewarm water (25-35° C.) for approx. 10 s per tooth without further mechanical action. The tooth was then stored in tap water tempered to 23-37° C. until the application of the adhesive.

The teeth were then blow-dried with compressed air until no more water was visible on the surface. The etching agent was applied with a brush-like dental applicator ("microbrush"). In the case of paste-like formulations, the conditioning agent was applied with a syringe. The tooth surface to be adhesively bonded was covered with a continuous layer of the conditioning agent. The layer was allowed to rest on the tooth without agitation for the scheduled dwell time. After a dwell time of 15 to 30 s, the conditioning agent was rinsed off with the water jet of a dental unit until no more residues were visible. After the rinsing, the etched dentin surface was dried according to the method indicated in Table 2.

Thereafter, two drops of the respective adhesive were placed on a mixing plate and applied to the pre-treated tooth surface with a microbrush. The adhesive was used in accordance with the manufacturer's instructions for use as described below. The adhesive was then blown with a stream of air, which was weak at first and then getting increasingly stronger, from a distance of approx. 2-8 cm until a film which was immobile under the strong stream of air had formed. This adhesive layer was then cured for 10 s with a light-polymerization device (Bluephase Style; Ivoclar Vivadent).

The teeth prepared in this way were introduced into the Ultradent application device with the prepared side upwards and were fixed in the application mould by slightly tightening the securing screws. Then the filling composite to be used (Tetric EvoCeram BulkFill; Ivoclar Vivadent) was applied through the opening of the application mould in a layer thickness of 1-1.5 mm and then cured for 20 s by means of exposure to light by a Bluephase Style. After the polymerization had finished, the retaining screws could be loosened and the composite test piece could be removed from the clamping device by means of gentle pressure with a composite condenser on the composite plug. For each series of measurements, 5 test pieces were prepared and stored in tap water for 24 h at 37±1° C. prior to the measurement of the adhesion.

Before the actual adhesion measurement, the diameter of the composite plug was measured accurate to two decimal places with a slide gauge and this value was recorded in the evaluation software of the testing machine (testXpert; ZWICK-ROELL).

For the determination of the adhesive force, the ZWICK 010 universal testing machine (ZWICK-ROELL) was used. The test piece was fixed in the clamping device according to ISO 29022 with the cutting face downwards ("crown down") and then a shearing device was positioned such that the semicircular moulding thereof exactly gripped the composite plug and the shearing device rested flat against the tooth. On starting the measuring procedure, the shearing device was lowered by 1 mm/min and the test piece was thereby loaded with a shear stress parallel to the substrate surface until it breaks. The adhesive strength is calculated as the quotient of the breaking force being applied at break and the adhesive surface below the composite plug. The data are given in megapascals (MPa).

In addition to the absolute coefficients of adhesion, the investigations of the coefficients of adhesion also comprised the type of fracture on failure of the test pieces. Test pieces fail on shear loading either "cohesively" in the dentin or "adhesively" between dentin and adhesive. A cohesive fracture usually occurs during measurements on dentin according to ISO 29022 at coefficients of adhesion >20 MPa and indicates a direct contact between intact tooth structure and adhesive. Adhesive fractures, on the other hand, usually occur at coefficients of adhesion <20 MPa and indicate a separation layer (e.g. collapsed collagen) which is impermeable to the adhesive on the intact tooth structure.

In order to test the technical tolerance of the conditioning solutions according to the present invention vis-à-vis the established phosphoric acid, in some cases the wetness of the dentin surface was varied for investigations of the coefficients of adhesion before adhesive was applied by means of drying for different lengths of time. The following moisture levels were generated (Table 2):

TABLE 2

| Degrees of dryness (Dentin) | |
| --- | --- |
| Moisture level | Drying conditions |
| Wet | Blotting with damp paper towels (Precision Wipes; KimWip) |
| Dry | 5 s strong stream of air (4 bar) |
| Very dry | 10-15 s strong stream of air (4 bar) |

The shear bond strength values were determined according to the named ISO standard with the commercial dental adhesives Excite F (Ivoclar Vivadent AG) and Prime & Bond NT (Dentsply). The chosen adhesives are intended as total-etch adhesives for use on tooth surfaces etched with phosphoric acid and have the two solvents usual for these products (ExciTE F: ethanol, Prime&Bond NT: acetone). Both adhesives were used on etched tooth surfaces in accordance with the instructions for use provided by the manufacturer.

ExciTE F:

A layer of the adhesive was applied to the etched tooth surface with a microbrush, massaged in for 10 s with gentle pressure and then aerated with an air blower until an immobile film had formed. The latter was exposed to light with a light-polymerization device (Bluephase Style; Ivoclar Vivadent) for 10 s. A composite plug (Tetric EvoCeram BulkFill; Ivoclar Vivadent) was then grafted as described and the shear bond strength was measured.

Prime i Bond NT:

A continuous layer of the adhesive was applied to the etched tooth surface by microbrush. Should the tooth surface no longer glisten wetly after a dwell time of 20s, a further layer of adhesive was applied in accordance with the instructions for use. Aeration then took place with an air blower until a continuous, glistening film had formed. The latter was exposed to light with a light-polymerization device (Bluephase Style; Ivoclar Vivadent) for 10 s. Thereafter, as described, a composite plug (Tetric EvoCeram BulkFill; Ivoclar Vivadent) was grafted and the shear bond strength was measured. The results are summarized in Table 3.

TABLE 3

Shear bond strength values on dentin (24 h@37° C.)

Coefficients of adhesion in MPa
(fracture pattern)

| Solution | Adhesive | Wet | Dry | Very dry |
|---|---|---|---|---|
| EP[1] | Excite F | 28.7 ± 2.8 (4/5) | 12.9 ± 4.8 (0/5) | 8.3 ± 2.2 (0/5) |
| A | Excite F | 31.5 ± 5.2 (5/5) | 27.9 ± 5.0 (4/5) | 22.5 ± 4.8 (4/5) |
| B | Excite F | 28.7 ± 5.7 (5/5) | 25.8 ± 8.8 (3/5) | 27.2 ± 13.0 (3/5) |
| C | Excite F | — | 28.8 ± 3.1 (5/5) | — |
| D | Excite F | — | 22.2 ± 8.7 (4/5) | — |
| E | Excite F | 35.8 ± 9.2 (5/5) | 31.2 ± 6.0 (5/5) | 26.7 ± 5.8 (4/5) |
| F | Excite F | 27.5 ± 6.1 (5/5) | 30.4 ± 6.9 (3/5) | — |
| G | Excite F | 23.9 ± 4.4 (5/5) | 32.7 ± 4.9 (5/5) | — |
| H | Excite F | 30.6 ± 5.4 (5/5) | — | — |
| I | Excite F | 31.0 ± 5.6 (5/5) | 29.8 ± 4.3 (5/5) | — |
| J | Excite F | 22.2 ± 4.4 (5/5) | — | — |
| K | Excite F | 29.6 ± 5.1 (5/5) | — | — |
| L | Excite F | 33.6 ± 5.8 (5/5) | — | — |
| M | Excite F | 32.5 ± 6.7 (5/5) | — | — |
| N | Excite F | 37.9 ± 4.1 (5/5) | — | — |
| O | Excite F | 29.2 ± 7.3 (5/5) | — | — |
| P | Excite F | 28.5 ± 2.0 (5/5) | — | — |
| Q | Excite F | 30.7 ± 9.3 (5/5) | — | — |
| EP[1] | Prime& | 30.7 ± 3.5 (5/5) | 9.90 ± 3.4 (0/5) | — |
| F | Bond NT | 33.2 ± 5.7 (5/5) | 23.6 ± 3.2 (4/5) | — |
| I | | 34.6 ± 5.1 (5/5) | 25.5 ± 4.1 (3/5) | — |

[1]Email Preparator blue, Ivoclar Vivadent: 37% phosphoric acid (comparison example)

The data in Table 3 show, for the conditioning agents A-B and E-Q in the case of use on wet dentin, an equivalent effect to the conventional phosphoric acid and adequate adhesion results irrespective of the adhesive. When the dentin was dried more strongly or even over-dried, the coefficients of adhesion of the surfaces treated with phosphoric acid decreased significantly as expected. On the other hand, the conditioning agents A-G and I tested in this regard representatively were influenced little or not at all by the drying process.

Example 3

Determination of Adhesion to Tooth Enamel

The measurement of adhesion to tooth enamel was carried out analogously to Example 2. Since enamel, as an almost purely inorganic tissue, contains no collagen fibrils the drying time was not varied. Therefore, to test the enamel adhesion, only dry substrate was investigated; after rinsing off of the etching agent the surface was dried for approx. 5 s with a strong stream of air from a dental unit. The aim was to obtain the image of a chalky-white enamel surface which is familiar to a dentist. In order to test the effect of an etching period reduced to 15 s vis-à-vis the established standard of 30 s, both dwell periods were investigated for selected samples. The results for the enamel coefficients of adhesion are given in Table 4.

The enamel adhesion values shown in Table 4 are, irrespective of the tested adhesive, comparable to the conventional phosphoric acid for the conditioning agents A-Q within accuracy of measurements. Even values appearing lower because of fluctuations in the nature of the tooth substrate are high enough to ensure a clinically adequate bond. Because of the hardness of the substrate, enamel samples always fail adhesively, so that the type of failure (fracture pattern) was not noted here.

TABLE 4

Shear bond strength values on tooth enamel (24 h@37° C.)

| Solution | Adhesive | 30 s Etching time (MPa) | 15 s Etching time (MPa) |
|---|---|---|---|
| EP[1] | Excite F | 29.6 ± 4.7 | 27.2 ± 8.8 |
| A | Excite F | 25.8 ± 2.6 | 30.7 ± 4.6 |
| B | Excite F | 24.8 ± 5.8 | 33.5 ± 6.1 |
| D | Excite F | — | 29.2 ± 4.9 |
| E | Excite F | — | 28.8 ± 2.5 |
| F | Excite F | — | 24.1 ± 6.3 |
| G | Excite F | — | 23.5 ± 8.5 |
| H | Excite F | — | 25.2 ± 6.0 |
| I | Excite F | — | 28.3 ± 1.9 |
| J | Excite F | 20.9 ± 3.8 | — |
| K | Excite F | 33.0 ± 2.8 | — |
| L | Excite F | 26.2 ± 1.3 | — |
| M | Excite F | 30.8 ± 6.8 | — |
| K | Excite F | 26.7 ± 6.4 | — |
| O | Excite F | 30.0 ± 3.6 | — |
| P | Excite F | 20.7 ± 2.5 | — |
| Q | Excite F | 27.2 ± 7.3 | — |
| EP[1] | Prime & | 24.5 ± 6.5 | 17.8 ± 2.8 |
| F | Bond NT | 21.6 ± 3.4 | 28.2 ± 8.2 |
| I | | 31.0 ± 4.2 | 25.5 ± 6.6 |

[1]Email Preparator blue, Ivoclar Vivadent: 37% phosphoric acid (comparison example)

Example 4

Determination of the Margin Quality on Tooth Enamel

The margin quality, which is important for the evaluation of the enamel bond, was measured. The margin quality denotes the fault-free proportion of the junction between composite and tooth in a circular cavity in bovine teeth. If, e.g., defects such as cracks, bulges or gaps can be observed on 60% of the tooth-composite junction, the margin quality is 40%. The evaluation was carried out by scanning electron microscope (SEM) "VP DSM" (Zeiss, Germany).

For the determination of the margin quality, 5 test pieces were prepared for each series of measurements. The preparation of the cavity was carried out in each case with a diamond abrasive bur at 40,000 rpm accompanied by water cooling (diameter: 4 mm, depth: 2.5 mm). For this, a Komet No. 909/040 diamond abrasive bur (4 mm) served for the first drilling and a cylindrical diamond abrasive bur No. 2504 (1.9 mm, 25 μm) for the finishing. The etching agent (Solution B) was applied by microbrush to cover the cavity walls and allowed to work for 15 s without agitation. The etching agent was then rinsed off with a jet of water and the cavity surface was blow-dried with an air blower until chalky-white enamel became visible. The ExciTE F adhesive (Ivoclar Vivadent) was applied to the dried surface in accordance with the instructions for use, allowed to work, blow-dried and light-cured (Bluephase Style; Ivoclar Vivadent). The filling composite (Tetric EvoCeram; Ivoclar Vivadent) was then introduced into the cavity prepared in this way in 2 mm increments and each increment was light-cured before the next increment. Finally, the laid filling was polished (SiC paper, P600-grit, 1200-grit, 2500-grit, 0.5 μm Masterprep (Buehler)/polishing disc (4000-grit)) and stored for 48 h in distilled water at 37° C.

To prevent vacuum artefacts during the subsequent examination by scanning electron microscope (SEM), the examination was carried out on replicas of the test pieces (impression silicone: "Virtual extra light body", fast set; pressure vessel; 2 bar). These impressions were cast after curing with epoxy resin (Stycast) in order to prevent the formation of bubbles through evaporation of the silicone in the vacuum. Lastly, contact silver was applied to these replicas in order to prevent charging in the electron beam.

The analysis of the marginal seal quality was carried out by SEM at 300 times magnification. The entire margin of the cylindrical cavity (Ø 4 mm) was divided into 40 margin sections and the percentage proportion of regular margin was allocated to each margin section. The sum of the percentages was then divided by the number of margin sections (=40). A margin section was judged to be regular if it presented itself without recognizable gap, irregularity or margin fracture. There is a good margin quality if the proportion of defect-free margin is greater than 70% on average. The results of this examination for conditioning agent B and the ExciTE F adhesive are given in Table 5.

TABLE 5

Enamel margin quality in the case of a Class I cavity

| Etching solution | Adhesive | Proportion of perfect margin |
|---|---|---|
| Email Preparator blue[1] | Excite F | 80-90 |
| B | | 80-90 |

[1]Email Preparator blue, Ivoclar Vivadent: 37% phosphoric acid (comparison example)

As Table 5 shows, conditioning agent B gives a comparable margin quality to the conventional procedure using 37% phosphoric acid.

Example 5

Inhibition of Collagen Degradation

To investigate the influence of zirconium salt solutions on the collagen degradation induced by matrix metalloproteinases (MMPs) slices of bovine tooth with a thickness of 1 mm were prepared with a precision circular saw. The tooth slices were completely demineralized by being placed in 2M HCl at room temperature, and then washed acid-free with citrate buffer.

To investigate the etching gel effect on the enzymatic degradation of collagen, collagenase type I as is used in the "Collagenase Substrate Kit" (Fluka; No. 27672/27670) was used as MMP-representative.

Reference samples were not treated further after this washing step but were investigated directly. Test samples, on the other hand, were immersed for 60 s in 1% or 2% zirconyl chloride solution and then carefully rinsed with distilled water. The blank test was treated neither with collagenase nor with the zirconium salt solution.

The collagen samples were placed in Petri dishes and overlaid with a buffered solution of the type I collagenase. In the case of the samples not treated with the zirconium salt solution, incubation of the samples at 37° C. accompanied by gentle agitation using a laboratory shaker led to enzymatic degradation of the demineralized tooth slices. FIGS. 1 to 4 show the results determined in the case of this test.

FIG. 1 shows the blank test without collagenase and without zirconium salt. Even after 48 hours of storage no change is detectable in the demineralized tooth slice, i.e. the collagen was not degraded.

Figure 2:
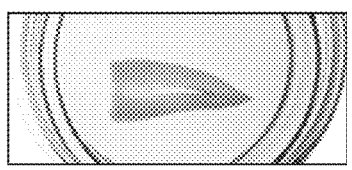
FIG. 2 shows a demineralized tooth slice after the addition of type I collagenase. Within 48 h, the collagenase effects an almost complete degradation of the collagen matrix.
Figure 2:
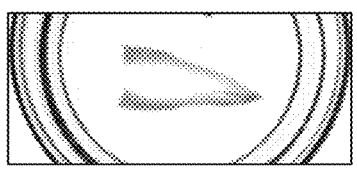
Figure 2:
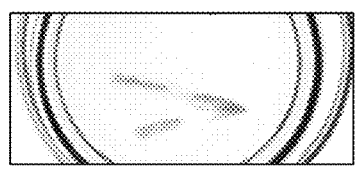

FIG. 2 shows that the addition of collagenase within 48 h leads to an almost complete degradation of the demineralized tooth slice. Significant degradation is already detectable after 24 h.

Figure 3:
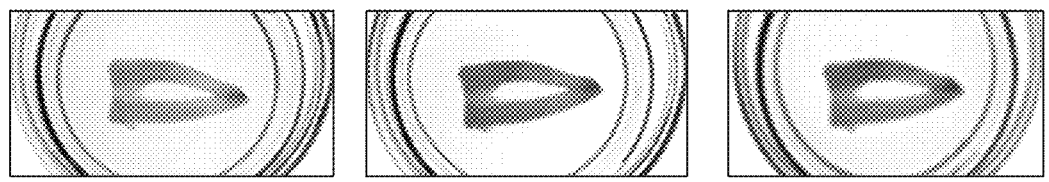
FIG. 3 shows a demineralized tooth slice which was immersed in a 2% zirconyl chloride (ZrOCl2) solution for 60 s before the collagenase treatment.
Figure 4:
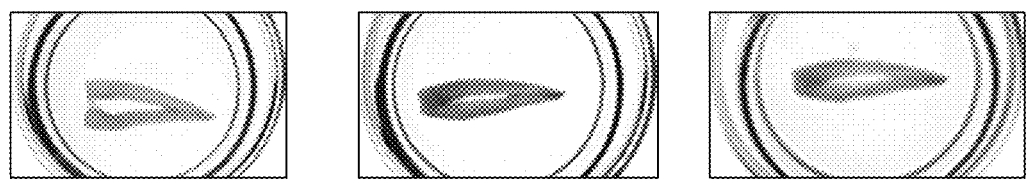
FIG. 4 shows a demineralized tooth slice which was immersed in 1% zirconyl chloride solution. Here too, the degradation of the collagen matrix is completely inhibited.

In FIGS. 3 and 4 it can be seen that even brief contact of dentinal collagen with a zirconium salt solution leads to a stabilization against enzymatic degradation. Even after 48 h, no degradation was visible in the case of zirconium-treated samples.

Example 6

Determination of the Etching Pattern on Enamel and Dentin

In order to prove the formation of a microretentive etching pattern by means of the conditioning solution according to the present invention, bovine enamel and bovine dentin were contacted with the formulations from Example 1, rinsed with water after the scheduled dwell time and the surface was examined in a scanning electron microscope. The conventionally used phosphoric acid served as comparison. Irrespective of the etching agent, the dwell time on dentin was 15 s and on enamel 15 to 30 s. The results at identical magnification are represented in FIGS. 5 to 21.

Figure 5:
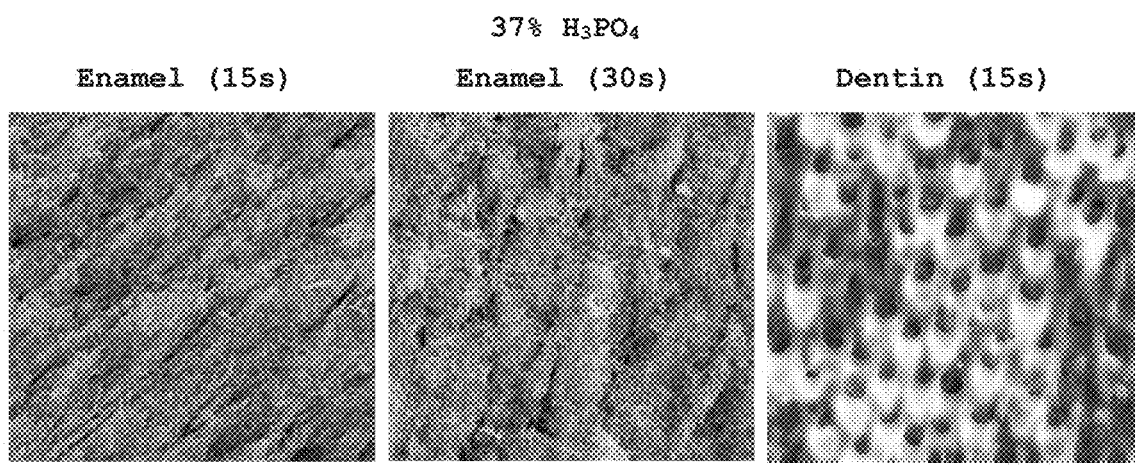
FIG. 5 shows the etching pattern on bovine tooth enamel and bovine dentin after etching with 37% phosphoric acid for 30 s and 15 s.
Figure 6:
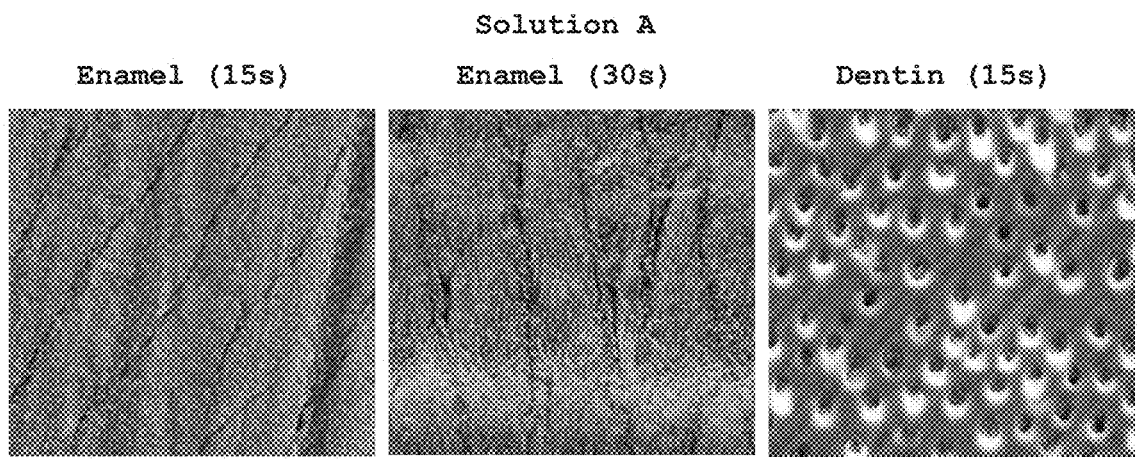
FIG. 6 shows the etching pattern on bovine tooth enamel and bovine dentin after etching with a 4% solution of ZrOCl2 in a 1:1 mixture of water and glycerol (Solution A) for 30 s and 15 s.
Figure 7:
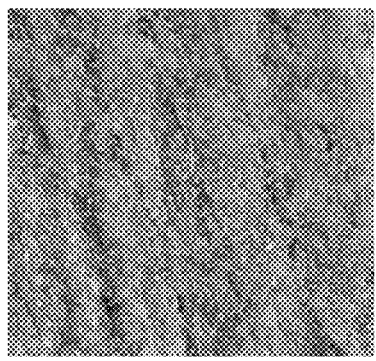
FIG. 7 shows the etching pattern on bovine tooth enamel and bovine dentin after etching with a 4% solution of Zr(SO4)2 in a 1:1 mixture of water and glycerol (Solution B) for 30 s and 15 s.
Figure 7:
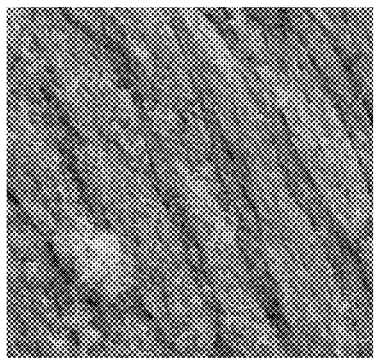
Figure 7:
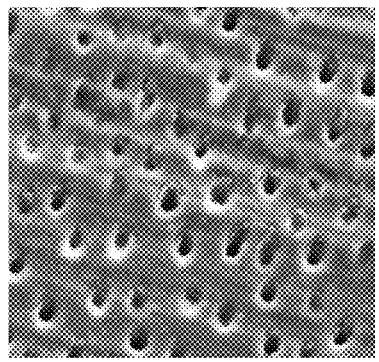
Figure 8:
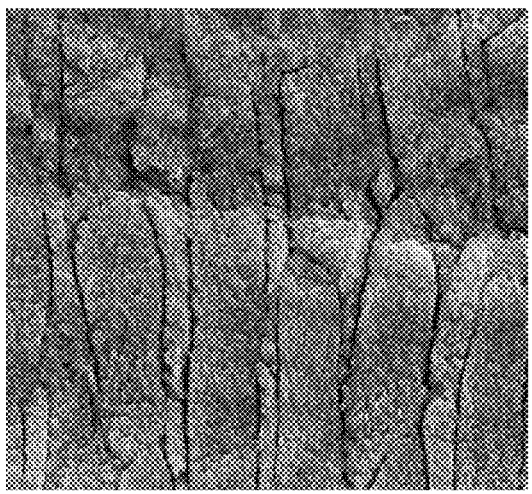
FIG. 8 shows the etching pattern on bovine tooth enamel and bovine dentin after etching with a 4% solution of ZrO(NO3)2 in a 1:1 mixture of water and glycerol (Solution D) for 15 s.
Figure 8:
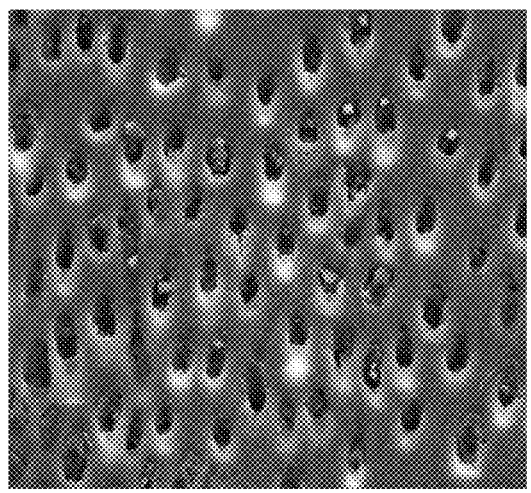
Figure 9:
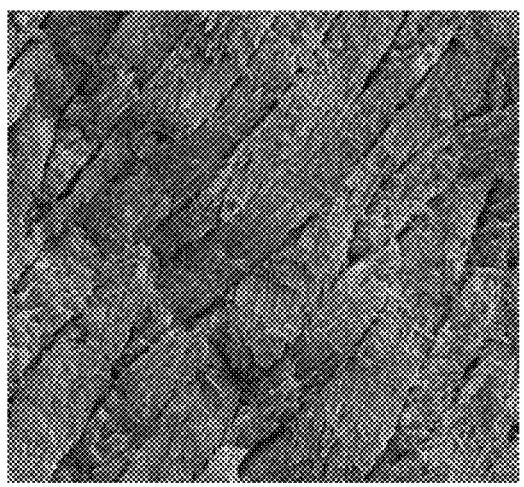
FIG. 9 shows the etching pattern on bovine tooth enamel and bovine dentin after etching with a 6% solution of ZrO(NO3)2 in water (Solution E) for 15 s.
Figure 9:
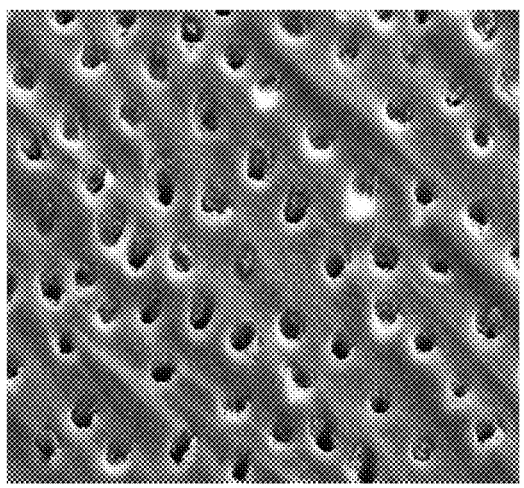
Figure 10:
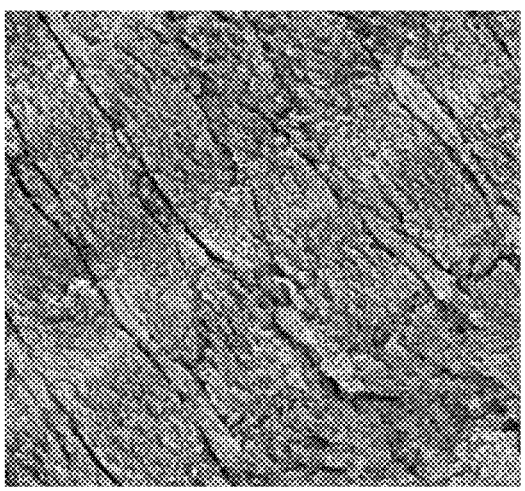
FIG. 10 shows the etching pattern on bovine tooth enamel and bovine dentin after etching with a 10% solution of ZrO(NO3)2 in a 1:1 mixture of water and glycerol (Solution F) for 15 s.
Figure 10:
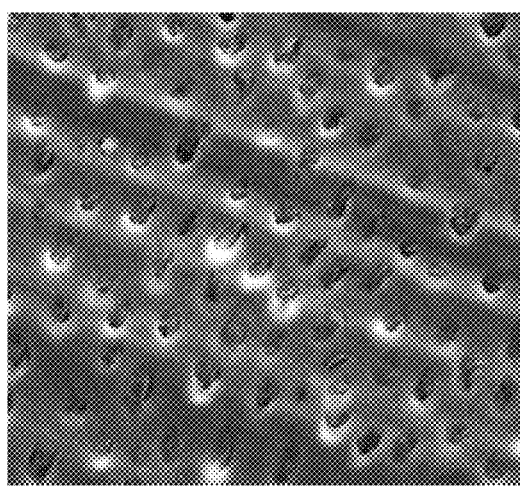
Figure 11:
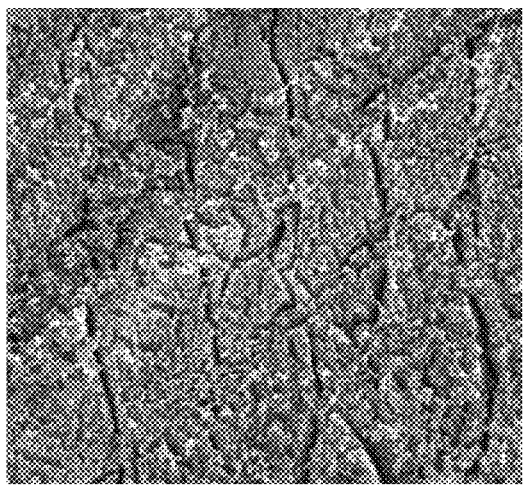
FIG. 11 shows the etching pattern on bovine tooth enamel and bovine dentin after etching with a 15% solution of ZrO(NO3)2 in a 1:1 mixture of water and glycerol (Solution G) for 15 s.
Figure 11:
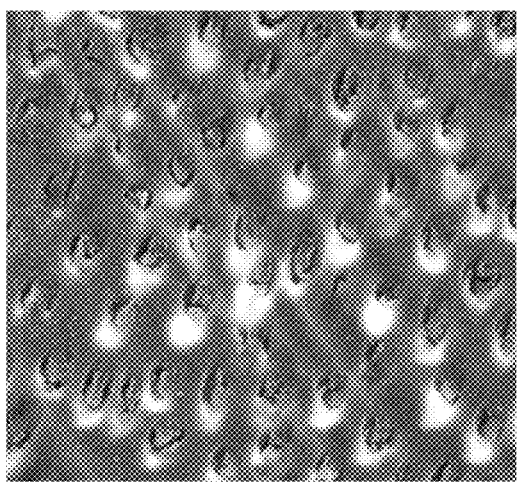
Figure 12:
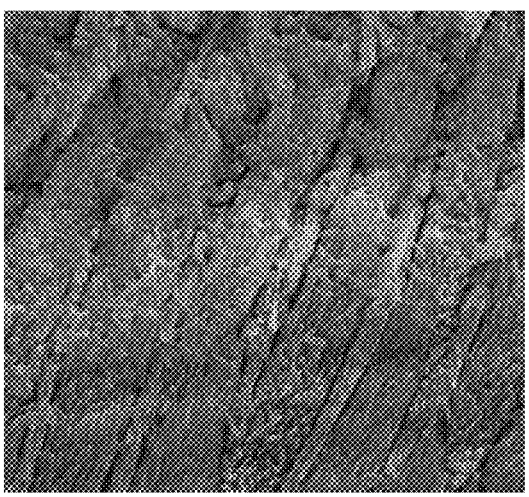
FIG. 12 shows the etching pattern on bovine tooth enamel and bovine dentin after etching with a 10% solution of ZrO(NO3)2 in a 1:1 mixture of water and PEG 400 (Solution H) for 15 s.
Figure 12:
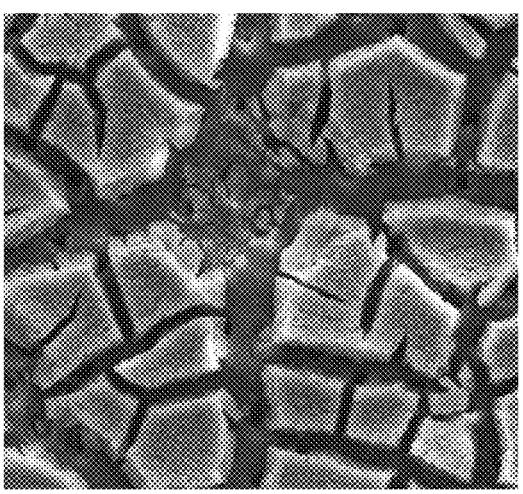
Figure 13:
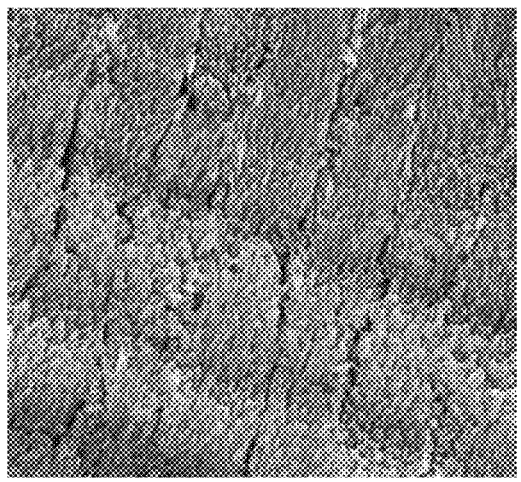
FIG. 13 shows the etching pattern on bovine tooth enamel and bovine dentin after etching with a 10% solution of ZrO(NO3)2 in a mixture of water, glycerol, thickener and pigment (Solution I) for 15 s.
Figure 13:
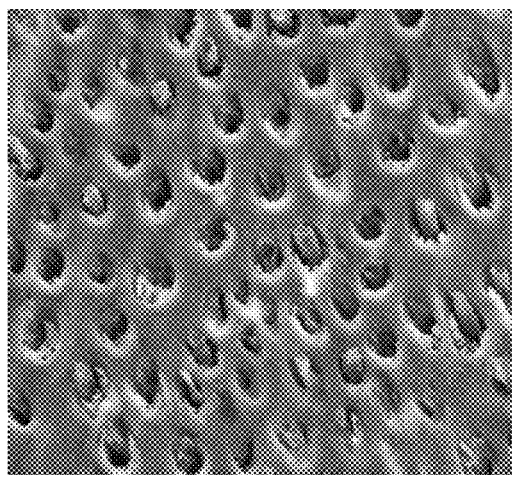
Figure 14:
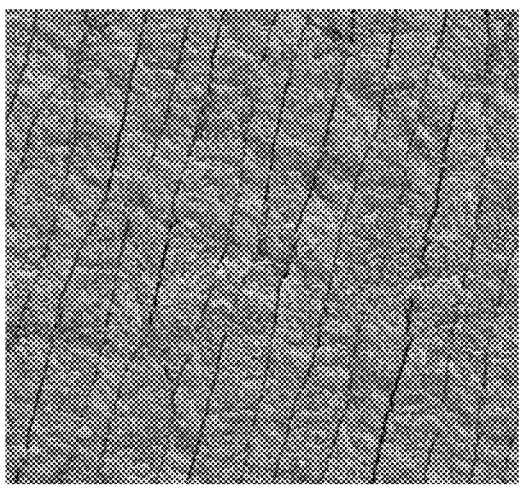
FIG. 14 shows the etching pattern on bovine tooth enamel and bovine dentin after etching with a 0.5% solution of TiOSO4 in a mixture of water and glycerol (Solution J) for 30 s and 15 s.
Figure 14:
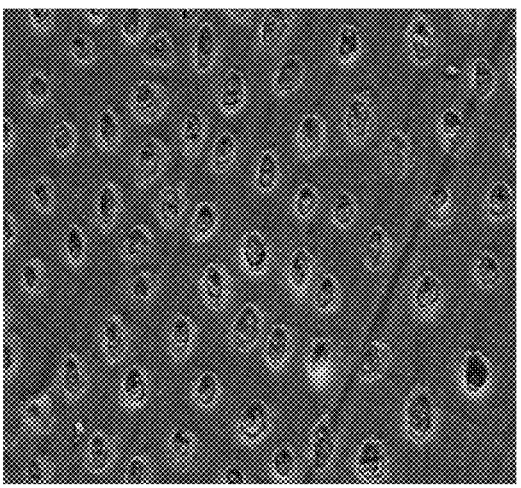
Figure 15:
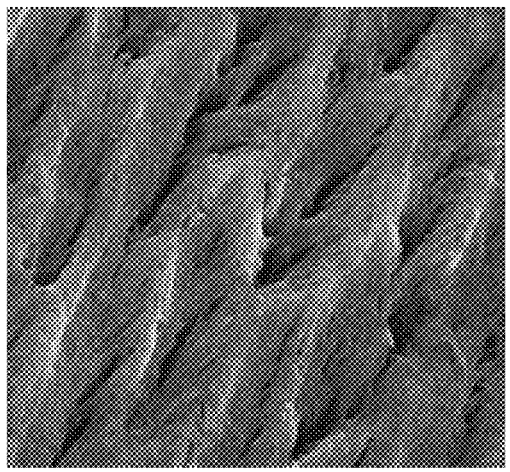
FIG. 15 shows the etching pattern on bovine tooth enamel and bovine dentin after etching with a 4% solution of SnCl4 in water (Solution K) for 30 s and 15 s.
Figure 15:
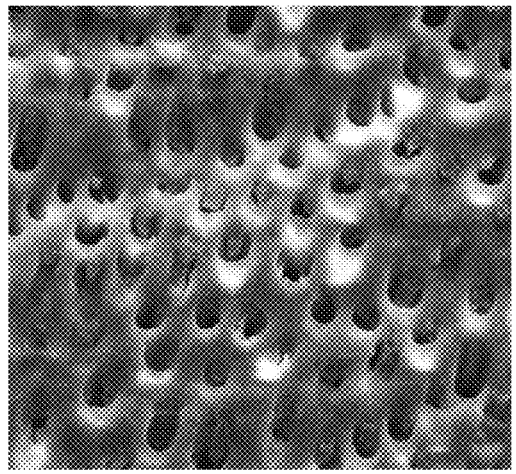
Figure 16:
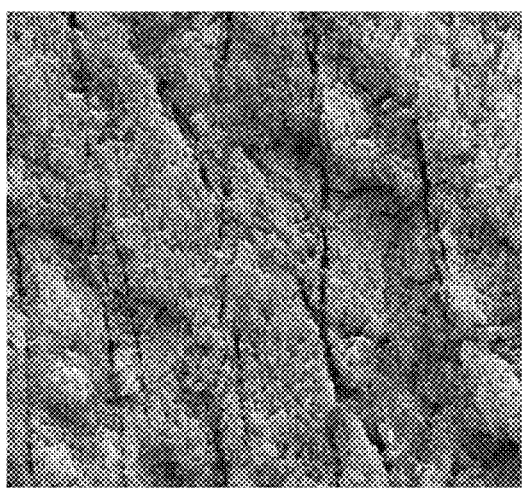
FIG. 16 shows the etching pattern on bovine tooth enamel and bovine dentin after etching with a 2% solution of Bi(NO3)3 in water (Solution L) for 30 s and 15 s.
Figure 16:
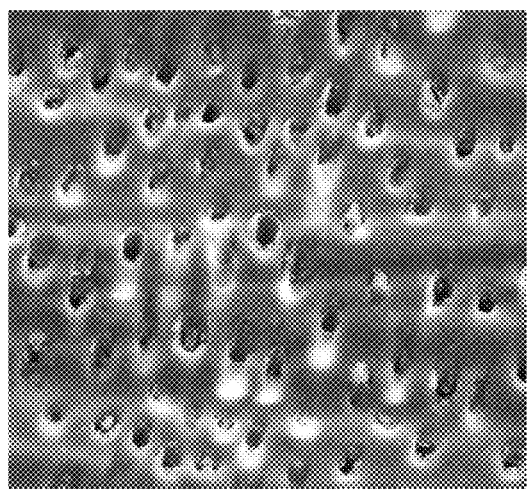
Figure 17:
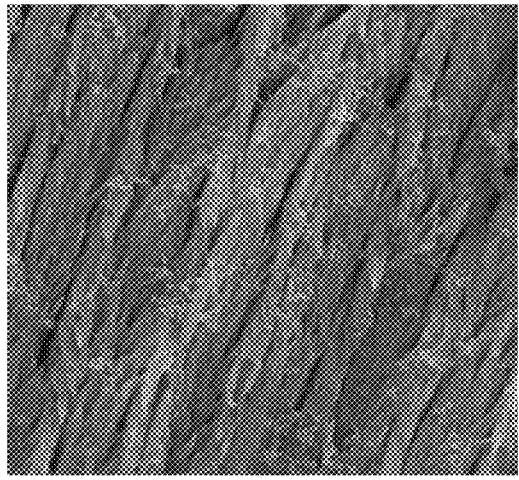
FIG. 17 shows the etching pattern on bovine tooth enamel and bovine dentin after etching with a 4% solution of Hf(SO4)2 in water (Solution M) for 30 s and 15 s.
Figure 17:
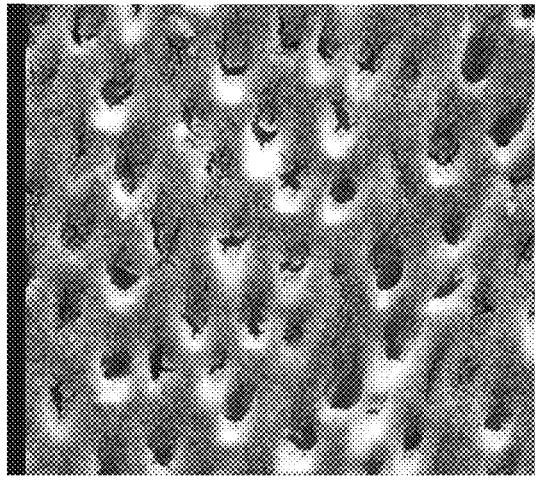
Figure 18:
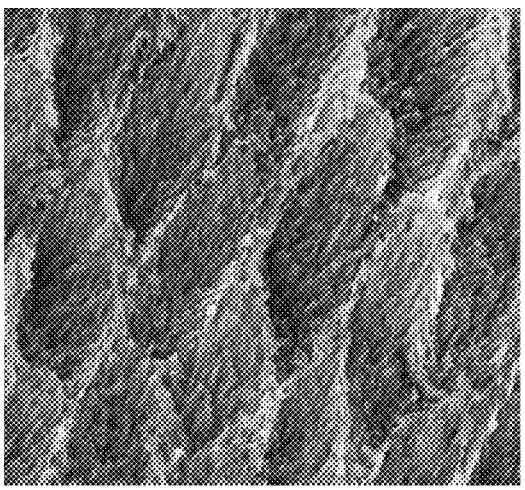
FIG. 18 shows the etching pattern on bovine tooth enamel and bovine dentin after etching with a 4% solution of HfCl4 in water (Solution N) for 30 s and 15 s.
Figure 18:
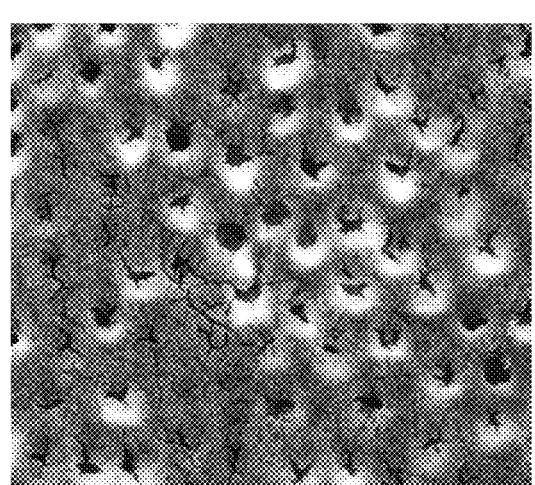
Figure 19:
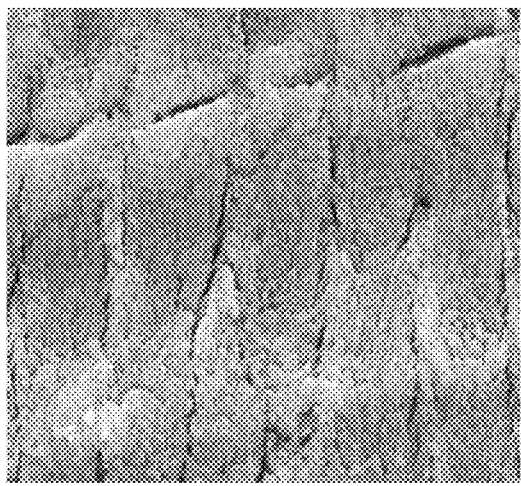
FIG. 19 shows the etching pattern on bovine tooth enamel and bovine dentin after etching with a solution comprising 6% ZrO(NO3)2 and 4% ZnSO4 in water (Solution O) for 30 s and 15 s.
Figure 19:
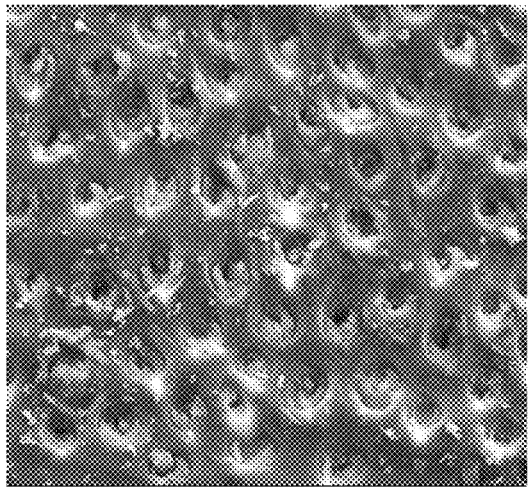
Figure 20:
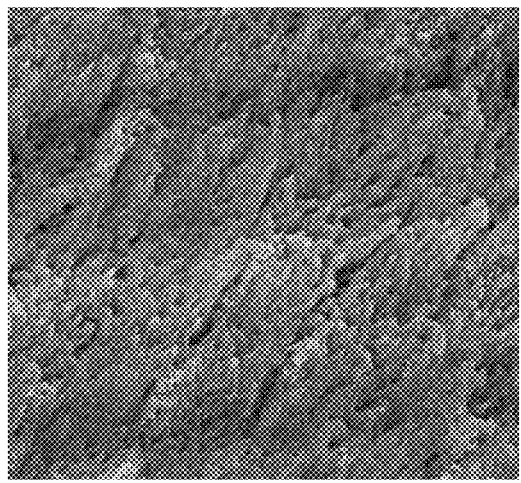
FIG. 20 shows the etching pattern on bovine tooth enamel and bovine dentin after etching with a solution comprising 6% ZrO(NO3)2 and 4% CuSO4 in water (Solution P) for 30 s and 15 s.
Figure 20:
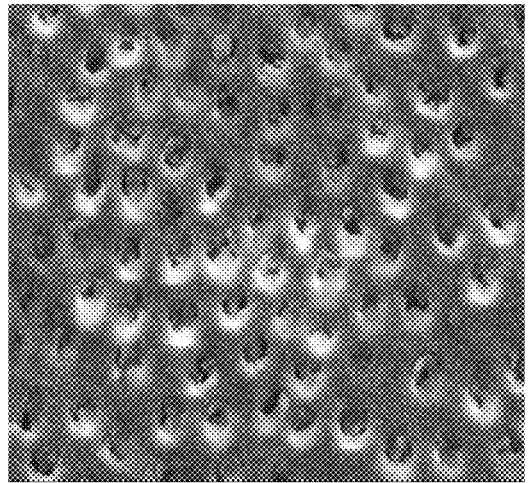
Figure 21:
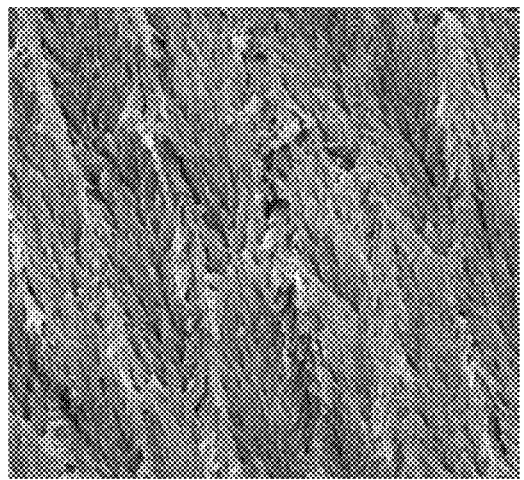
FIG. 21 shows the etching pattern on bovine tooth enamel and bovine dentin after etching with a solution comprising 6% ZrO(NO3)2 and 4% Al2(SO4)3 in water (Solution Q) for 30 s and 15 s.
Figure 21:
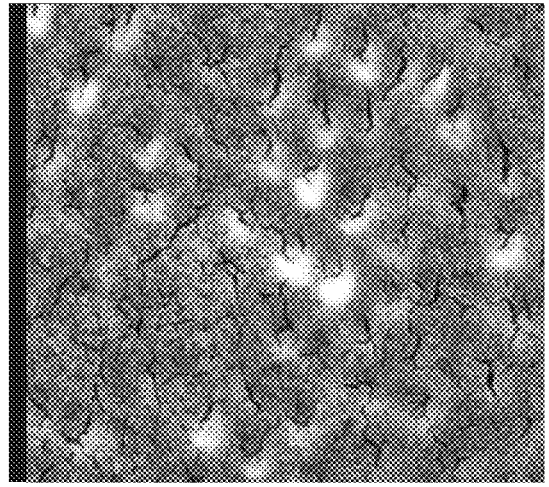

FIGS. 5 to 21 show a significant difference between phosphoric acid and the conditioning agents according to the present invention for dentin. Thus, already after 15 s, phosphoric acid effects an opening of all tubules by removal of the smear layer and significant demineralization phenomena, recognizable on white faces, which form in the electron beam as a result of the electrostatic charging of the tubule margins thinly etched by phosphoric acid and thus levelling out thinly (FIG. 5).

In the case of the use of the conditioning agents according to the present invention (FIGS. 6-21), on the other hand, the tubules remain largely sealed just below the dentin surface. Unlike after treatment with phosphoric acid, demineralization phenomena of over-etched tubule margins leading to electrostatic charging are barely visible. An over-etching of the dentin by the formulations according to the present invention can therefore be excluded.

In contrast to dentin, FIGS. 5-21 show no significant difference between phosphoric acid and the conditioning agents according to the present invention for enamel. All metal salt solutions led to the formation of a retentive etching pattern on the enamel which ensures a good bonding effect to the applied adhesive in all investigated cases.

The invention claimed is:

1. A conditioning agent for teeth comprising an aqueous solution which comprises 0.5 to 25 wt.-% of one or more transition and/or main group metal salts, wherein the transition and/or main group metal salt is a salt of $Zr^{4+}$, $Hf^{4+}$, $Ti^{4+}$ or $Sn^{4+}$.

2. The conditioning agent according to claim 1, wherein the transition or main group metal salt comprises as anion $Cl^-$, $Br^-$, $I^-$, $NO_3^-$, $SO_4^{2-}$, optionally as mixed salts with oxoanions.

3. The conditioning agent according to claim 1, which comprises as transition and/or main group metal salt $ZrOCl_2$, $ZrO(NO_3)_2$, $Zr(SO_4)_2$, $Hf(SO_4)_2$, $HfCl_4$, $Hf(NO_3)_4$, $TiOSO_4$, $SnCl_4$ or a mixture of these salts.

4. The conditioning agent according to claim 1, which additionally comprises a further metal salt which is selected from the salts of $Cu^{2+}$, $Zn^{2+}$, $Al^{3+}$ and mixtures thereof.

5. The conditioning agent according to claim 4, which additionally comprises $Al(NO_3)_3$, $CuSO_4$, $ZnSO_4$ or a mixture thereof.

6. The conditioning agent according to claim 1, wherein the metal ion is $Zr^{4+}$, $Hf^4$ or $Ti^{4+}$.

7. The conditioning agent according to claim 6, wherein the transition or main group metal salt comprises as anion $Cl^-$, $Br^-$, $I^-$, $NO_3^-$, $SO_4^2$, optionally as mixed salts with oxoanions.

8. The conditioning agent according to claim 6, which comprises as transition and/or main group metal salt $ZrOCl_2$, $ZrO(NO_3)_2$, $Zr(SO_4)_2$, $Hf(SO_4)_2$, $HfCl_4$, $Hf(NO_3)_4$, $TiOSO_4$ or a mixture of these salts.

9. The conditioning agent according to claim 6, which additionally comprises a further metal salt which is selected from the salts of $Cu^{2+}$, $Zn^{2+}$, $Al^{3+}$, $Sn^{4+}$ and mixtures thereof.

10. The conditioning agent according to claim 9, which comprises as a further metal salt $Al(NO_3)_3$, $CuSO_4$, $ZnSO_4$, $SnCl_4$ or a mixture thereof.

11. The conditioning agent according to claim 1, which contains no added acid.

12. The conditioning agent according to claim 1, which comprises 2 to 15 wt.-% transition and/or main group metal salt, 36 to 98 wt.-% water and 0 to 49 wt.-% organic solvent.

13. The conditioning agent according to claim 1, which comprises as organic solvent glycerol, ethanol, ethylene glycol, propylene glycol, propanediol, butanediol and polyethylene glycol or a mixture thereof.

14. The conditioning agent according to claim 1, which comprises 4 to 10 wt.-% transition and/or main group metal salt, 42 to 96 wt.-% water and 0 to 48 wt.-% organic solvent.

* * * * *